US008467059B2

(12) United States Patent
Killinger et al.

(10) Patent No.: US 8,467,059 B2
(45) Date of Patent: Jun. 18, 2013

(54) DEEP-UV LED AND LASER INDUCED FLUORESCENCE DETECTION AND MONITORING OF TRACE ORGANICS IN POTABLE LIQUIDS

(75) Inventors: Dennis K. Killinger, Temple Terrace, FL (US); Anna Sharikova, Ann Arbor, MI (US); Vasanthi Sivaprakasam, Washington, DC (US)

(73) Assignee: University of South Florida, Tampa, FL (US)

( * ) Notice: Subject to any disclaimer, the term of this patent is extended or adjusted under 35 U.S.C. 154(b) by 245 days.

(21) Appl. No.: 12/887,948

(22) Filed: Sep. 22, 2010

(65) Prior Publication Data
US 2012/0001094 A1    Jan. 5, 2012

Related U.S. Application Data

(63) Continuation-in-part of application No. 11/926,196, filed on Oct. 29, 2007, now Pat. No. 7,812,946.

(60) Provisional application No. 60/863,249, filed on Oct. 27, 2006.

(51) Int. Cl.
*G01N 21/25*      (2006.01)
*G01N 21/64*      (2006.01)

(52) U.S. Cl.
USPC ..................................... 356/417; 250/461.1

(58) Field of Classification Search
USPC ..................................... 356/417; 250/461.1
See application file for complete search history.

(56) References Cited

U.S. PATENT DOCUMENTS

| 4,076,420 | A | * | 2/1978 | De Maeyer et al. | ............ 356/73 |
| 5,894,347 | A | * | 4/1999 | MacDonald | .................. 356/317 |
| 6,042,785 | A | * | 3/2000 | Harju | .............................. 422/52 |
| 6,475,803 | B1 | | 11/2002 | Ueno et al. | |
| 6,541,272 | B1 | | 4/2003 | Mitra | |
| 7,552,617 | B2 | * | 6/2009 | Danilchik | .................... 73/23.41 |

OTHER PUBLICATIONS

Killinger, Dennis et al., Water Monitoring with Laser Fluorescence, OPN Jan. 2006, p. 35-39, www.osa-opn.org.
Pulse of the Planet Web site on fresh water usage: www.pulseplanet.com/archive/Jan00/2057.html.

(Continued)

*Primary Examiner* — Roy M Punnoose
(74) *Attorney, Agent, or Firm* — Nilay J. Choksi; Ronald E. Smith; Smith & Hopen, P.A.

(57) ABSTRACT

An apparatus for measuring fluorescence of potable liquids contained within an optical quartz cell includes a deep UV laser or a compact UV LED that generates a light beam. A UV blocking and visible light transmitting optical filter reduces out-of-band emission from the LED. The optical quartz cell is between a pair of plane mirrors so that light from the light source travels through it several times. A concave mirror collects a fluorescence signal and has a common optical axis with a lens. The common optical axis is normal to an optical axis of the light beam. The concave mirror and lenses are positioned on opposite sides of the optical quartz cell. A fluorescence detector is in optical alignment with the concave mirror and the lens. A boxcar averager is in electrical communication with the fluorescence detector. Optical wavelength selection of the fluorescence emission uses optical filters or a spectrometer.

12 Claims, 14 Drawing Sheets

OTHER PUBLICATIONS

Clescerl, L.S., Greenberg, A.E., Eaton, A.D., Standard Methods for Examination of Water and Wastewater, Am. Public Health Assoc., 20th Ed., 1999.

Coble, P.G., Characterization of Marine and Terrsestrial DOM in Seawater Using Excitation-Emission Matrix Spectroscopy, Marine Chemistry 51, p. 325-46, 1996.

Global Trends 2015, National Intelligence Council Report, #0441-015-00211-2, Dec. 2000.

Goodson, A. et al., Survey of Bisphenol-A and Bisphenol-F in Canned Foods, Food Add. Contam. 19, 796-802, 2002.

Sivaprakasam, V. and Killinger, D.K., Effects of Polarization and Geometrical Factors on Quantitative Laser-Induced Fluorescence-to-Ramen Intensity Ratios of Water Samples and a New Calibration Technique, J. Opt. Soc. Am. B 20, 1980 (2003).

Sivaprakasam, V. and Killinger, D.K., Tunable Ultraviolet Laser-Induced Fluorescence detection of Trace Plastics and Dissolved Organic Compounds in Water, Applied Optics, 42, 6739, 2003.

Sivaprakasam, V. et al., Development and Initial Calibration of a Portable Laser Induced Fluorescence System Used for in Situ Measurements of Trace Plastics and Organics in Seawater and the Gulf of Mexico, Applied Optics, 42, 6747, 2003.

MacLusky, N.J. et al., The Environmental Estrogen Bisphenol-A Inhibits Estradiol-Induced Hippocampal Synaptogenesis, Environmental Health Perspectives, 113, 647-679, 2005.

* cited by examiner

DEEP-UV LED AND LASER INDUCED FLUORESCENCE DETECTION AND MONITORING OF TRACE ORGANICS IN POTABLE LIQUIDS

CROSS REFERENCE TO RELATED APPLICATIONS

This application is a continuation-in-part and claims priority to pending U.S. patent application Ser. No. 11/926,196, entitled "Deep-UV Led and Laser Fluorescence Apparatus for Monitoring Water Quality," filed Oct. 29, 2007, which claims priority to U.S. provisional patent application No. 60/863,249, entitled "Deep-UV LED and Laser Fluorescence Apparatus for Monitoring Water Quality," filed Oct. 27, 2006 by the same inventors, the contents of which are herein incorporated by reference.

BACKGROUND OF THE INVENTION

1. Field of the Invention

This invention relates to deep-UV laser and LED induced fluorescence to detect and monitor in real-time trace species found in potable liquids such as drinking water, wines, juices, and distilled spirits.

2. Description of the Prior Art

Conventional tools do not include real-time, easy to use monitoring instrumentation for detection and monitoring of trace species and related quality parameters for water samples and other water related liquids.

Conventional methods for the analysis of drinking water and many other liquids often call for the use of reagents and may require extensive sample preparation. For the case of water supplies and water treatment plants, this analysis is usually carried out once every few days or weeks. Most of the analysis is usually conducted using classical analytical chemical techniques, such as mass spectrometry, liquid chromatography, or fluorescence based or tagged reagents. These analytical techniques are sensitive and provide accurate assessment of the chemistry related to the quality of the liquids. However, they often take considerable time and are usually not performed in real-time, especially for the case of a flowing process line. On the other hand, previous fluorescence spectroscopic measurements of ocean water showed that deep-UV excitation of naturally occurring organic compounds in water can yield significant and unique fluorescence signals in the near UV to visible wavelength range without the need to use additional reagents or sample preparation. Accordingly, there is a need for deep-UV laser-induced-fluorescence techniques for the detection of trace species in water and other liquids to use the natural fluorescence of trace species in water or liquid samples to provide readings within the time span of a few seconds.

Most approaches for monitoring water quality in water processing plants are based on "wet" chemistry techniques that require the addition of other chemicals to water samples. Many use gas chromatography or liquid chromatography followed by laser fluorescence detection in a reagent capillary tube, while others use reagents that change pH, color, or other physical characteristics depending upon the concentration of selected or trace species. Although useful in the lab, these techniques work less well in the field, where reagents are difficult to replace and harsh conditions may degrade them.

Earlier laser-induced fluorescence (LIF) studies of water have used either blue-green (513.5 nm) argon ion lasers or doubled (535 nm) Nd:YAG lasers for excitation, as well as staining reagents for improving the contrast of detected organisms. Studies that have relied on natural or auto-fluorescence from water have generally not been as successful as those that have used fluorescent dyes. This is perhaps because blue-green wavelengths do not sufficiently separate between the emission spectral peaks due to trace organics, Raman emission from water, and that due to the excitation or interfering background spectra.

As a result, few previous LIF studies have drawn on the natural fluorescence of trace species in the water. The novel system therefore employs a deep-UV laser source near 220 nm-300 nm for excitation to overcome some of the limitations of the natural fluorescence approach. The resultant fluorescence emission from the organics is well separated from the excitation wavelength and from water Raman emission.

There is a need for a reagentless, deep UV (220 nm-300 nm) laser-induced-fluorescence (LIF) system for detecting contaminates and potentially harmful substances in bottled and processed water and the ocean.

It is known that expensive laser-based fluorescence detection of dissolved organic compounds in drinking water is feasible. Previous work by the inventors has shown that laser induced fluorescence can be used for the detection of trace DOCs and leached plasticizers (such as Bisphenol-A, also known as BPA) in water and that different drinking water samples from different bottled water manufacturers show significant different levels of DOCs and/or plasticizers. Such prior art work appears in several research publications such as: (1) Tunable ultraviolet laser-induced fluorescence detection of trace plastics and dissolved organic compounds in water, Vasanthi Sivaprakasam and Dennis K. Killinger, Applied Optics 42, 6739 (2003), (2) Development and initial calibration of a portable laser induced fluorescence system used for in situ measurements of trace plastics and organics in seawater and the Gulf of Mexico, Vasanthi Sivaprakasam, Robert Shannon, Caiyan Luo, Paula G. Coble, Jennifer Boehme, and Dennis K. Killinger, Applied Optics 42, 6747 (2003), and (3) Water Monitoring with Laser Fluorescence, Dennis Killinger and Vasanthi Sivaprakasam, Invited Review, OSA Optics and Photonics News, p 35, January 2006

The 266 nm UV laser used for excitation in these published prior art studies by the authors and inventors cost $10,000. Accordingly, there is a need for a low cost, compact LED to replace the known expensive lasers.

Currently, no real time or reagentless laser-induced-fluorescence systems have been authorized for use by water treatment plants. However, for the past several years, some water agencies have been testing a selected range of UV absorption and fluorescence water monitoring instruments. One such device is a UV-visible (200 nm-750 nm) absorption instrument from S-CAN in Austria that can detect small changes in the optical absorption properties of water.

Another fluorescence-based test is used to monitor water for the *e-coli* bacteria. This involves growing a culture obtained from a water sample, using a fluorescence dye or stain, and counting the organisms by either visual microscopes or laser readers. Fluorescence is also used in liquid chromatography laser-induced fluorescence, or LC-LIF, a technique in which a capillary tube is used to separate the chemical species and a laser reads the separated column.

However, in view of the art considered as a whole at the time the present invention was made, it was not obvious to those of ordinary skill in this art how the identified needs could be met.

SUMMARY OF INVENTION

The long-standing but heretofore unfulfilled need for a compact, less expensive UV LED-based laser-induced fluorescence instrument to detect and monitor dissolved organic compounds or carbon, or both, in drinking water in real time is now met by a new, useful, and nonobvious invention that detects deep-UV (near 266 nm) laser and deep-UV LED excited fluorescence emission (near 450 to 500 nm) of the dissolved organic compounds, DOCs, and other related trace species in the water.

More particularly, the novel apparatus for measuring fluorescence of potable liquids contained within an optical quartz cell includes a deep UV light source that generates a light beam. The deep UV light source may be a UV laser or a compact UV LED. A UV blocking and visible transmitting optical filter is used to reduce the out-of-band emission from the LED. The optical quartz cell is disposed between a pair of plane mirrors so that light from the light source travels through the optical quartz cell several times. A concave mirror collects a fluorescence signal and has a common optical axis with a lens. The common optical axis is disposed normal to an optical axis of the light beam and the concave mirror and lens are positioned on opposite sides of the optical quartz cell. A fluorescence detector is disposed in optical alignment with the concave mirror and the lens and a gated integrator and boxcar averager is disposed in electrical communication with the fluorescence detector. An oscilloscope and a computer are in electrical communication with the gated integrator and boxcar averager. Optical wavelength selection of the fluorescence emission can be made using optical filters or a compact spectrometer.

The novel method for detecting trace levels of dissolved organic compounds in drinking water includes the steps of employing a deep ultraviolet (UV) light-emitting diode laser-induced fluorescence at sensitivity levels of several parts per trillion in real time. This provides a more compact and inexpensive excitation source, relative to a deep UV laser-induced fluorescence, for laser-induced fluorescence detection of dissolved organic compounds in water. The cost of the deep-UV LED (near 265 nm) is about $100.00, and consumes much less power and is more compact than the deep-UV 266 nm laser (cost of $10,000).

The deep UV light-emitting diode is preferably operated at an excitation near 266 nm and the laser-induced fluorescence is detected at an emission near 450 nm to 500 nm. Excitation in the UV up to wavelengths near 320 nm can be used for excitation, but optical filtering is less selective and the sensitivity is less than that obtained using wavelengths near 265 nm or less.

Optical absorption filters and optical bandpass filters are employed to reduce out-of-band light emitting diode (LED) emissions and to eliminate second order optical interference signals for the detection of a fluorescence signal near 450 nm to near 500 nm.

A modulated continuous wave LED excitation source is employed to produce detection sensitivity within a factor of twenty (20) to thirty (30) times relative to a pulsed (8.6 KHz) 266 nm laser source.

A pulsed (about 10 KHz PRF) LED source and a gated (100 ns) detection system is used to provide gated noise rejection of the fluorescence signal to obtain increased sensitivity and reduced background noise because the fluorescence lifetime of the dissolved organic compounds in water is about 50 ns.

Modulated continuous wave LEDs using a lock-in amplifier signal processing and pulsed LEDs using gated boxcar integrators are employed to optimize the dissolved organic compound fluorescence signals and improve the signal-to-noise ratio.

Grating spectrometers and silicon detectors arrays, or sets of optical filters in a sequential wheel arrangement with photomultiplier detectors, or both, are employed to detect the fluorescence emission.

The novel system has a sensitivity of about a few parts per trillion, which is several orders of magnitude better than conventional spectrofluorometers. It detects the presence of plastic resins and dissolved organic compounds in bottled drinking water, monitors real time changes in DOCs in drinking water processed by reverse osmosis, and tracks DOCs and river plumes in the Gulf of Mexico.

Conventional spectrofluorometers use Xenon lamps and excitation filtering spectrometers to produce the UV excitation beam, but their beam intensity is three to nine orders of magnitude less intense than that available with a laser or LED source.

Pulsed atomic emission lamps in the deep-UV (such as a low-pressure mercury lamp) and optical narrow-line filters may be used for the deep-UV excitation source in the fluorescence system. Such lamps are less intense than LEDs and lasers by several orders of magnitude, but provide sufficient excitation power if the DOC fluorescing concentrations is extremely large.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
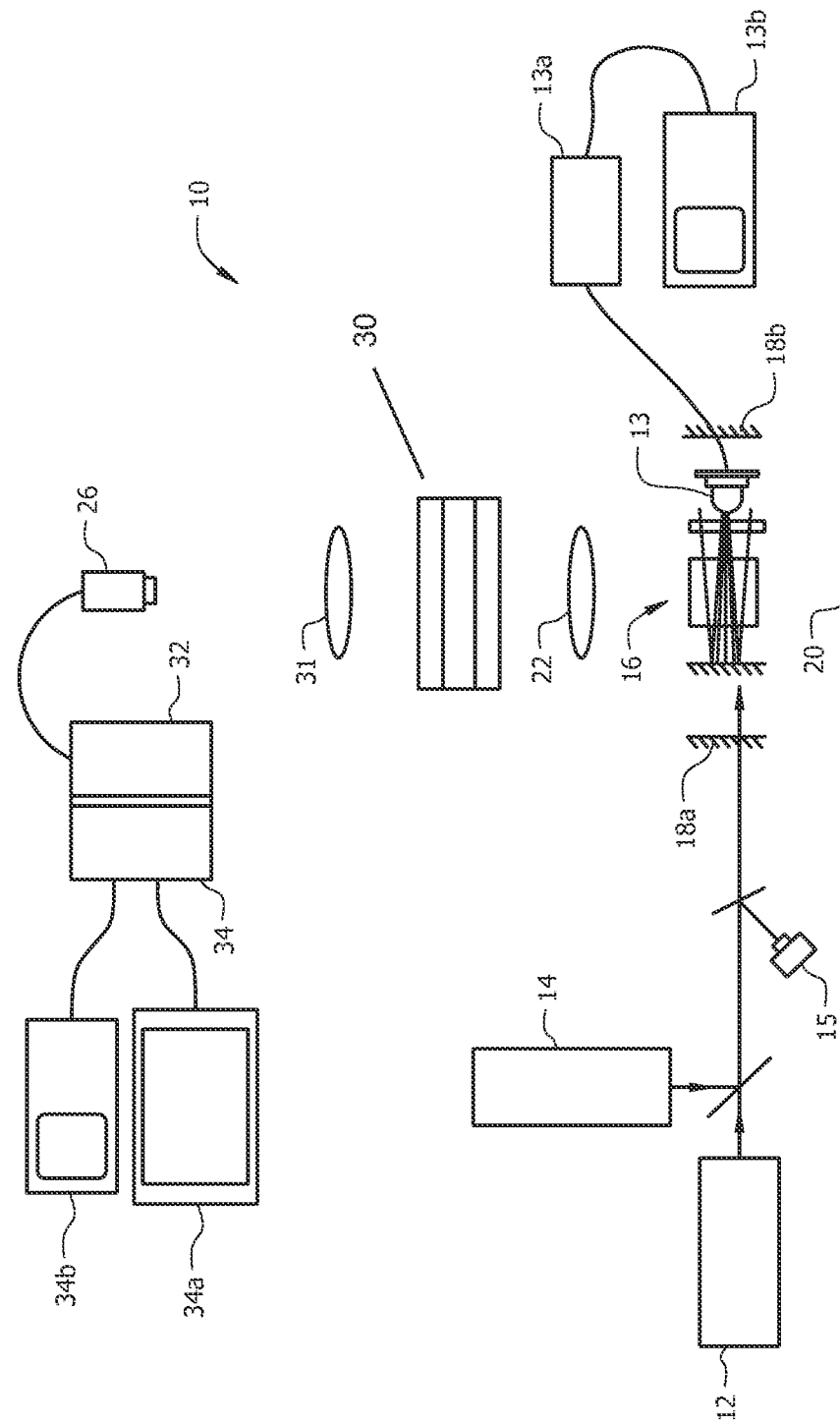
FIG. 1 is a schematic diagram of the novel apparatus.

This invention relates to the monitoring of water quality and the detection of trace dissolved organic compounds, leached plasticizers, or carbon (DOCs) in drinking water and other potable liquids.

More particularly, the novel deep-UV laser or LED induced fluorescence (LIF) system detects and monitors in real time levels of organics, dissolved organic compounds (DOC), colored dissolved organic matter (CDOM), and other trace species in drinking water, wines, juices, coffee, and distilled spirits. A similar system using a compact and inexpensive set of deep-UV Light-Emitting Diodes (LEDs) detects and monitors these trace species in water and water related drinks or samples.

The novel reagentless deep-UV laser and UV-LED induced fluorescence (LIF) system detects and continuously observes in real time trace levels of colored dissolved organic matter (CDOM) or dissolved organic compounds (DOCs) in water and distilled spirits, such as drinking water, and related water or alcohol based liquids with a sensitivity exceeding that of commercial spectrofluorometers. The novel system is used to detect parts per billion (ppb) trace levels of plasticizer Bisphenol-A (BPA) that have leached into drinking water, and to detect and monitor trace levels of DOCs within ocean currents. The novel LIF system also measures fluorescence of reverse osmosis processed water and different types of drinking water. These LED/LIF applications include additional water related samples, including humic acid samples, tannic acid and chlorinated water samples, juices, coffee, and several wines and distilled spirits.

The novel compact LIF system uses either frequency tripled or fourth harmonic diode pumped Nd:YAG lasers operating at 266 nm and 355 nm, or deep-UV LEDs (265 nm, 300 nm, 335 nm, and 355 nm) as UV excitations sources. The emitted fluorescence is measured over the range of 240-680 nm. Strong emissions near 450 nm are observed for the DOCs in water, and emission bands near 340 nm are evident from distilled spirits and wine.

One of the main advantages of using a deep-UV excitation wavelength, such as 266 nm, is that the emission fluorescence is separated in wavelength from the Raman emission of water (near 310 nm for 266 nm excitation), and thus yields greater sensitivity and wavelength selectivity than previous systems using lasers operating near 400 to 550 nm. Moreover, as a point of reference, the novel laser based LIF system has detection sensitivity for the fluorescence standard solution of quinine sulfate on the order of 0.1 ppb. The average laser power is approximately thirty (30) times that of the LED, but differences in the signal intensity due to the difference in the laser and LED excitation intensity are consistent with theory.

Deep-UV light emitting diodes (LEDs) are good alternative light sources for the novel LIF system, because they make the apparatus less expensive and more compact than conventional systems. This disclosure is directed toward the development of new optical spectroscopic measurement techniques having the potential to provide enhanced capabilities over conventional water monitoring and liquid analysis. The sensitivity of the novel system is in the sub-parts per billion for standard fluorescing compounds used in fluorescence research, such as quinine sulfate.

The sensitivity of the novel laser and LED induced fluorescence system is several orders of magnitude better than that of a conventional spectrofluorometer. Conventional spectrofluorometers often use UV lamps and wavelength selecting spectrometers for the emission source, and single or double monochromators with photo-multiplier tubes or CCD detecting arrays for fluorescence detection. The signal processing is typically conducted using a chopped CW beam and lock-in amplifier signal detection. The novel LIF system uses a high PRF (pulse-repetition-frequency) laser running at about 8,000 pulses/second as the excitation source (or a pulsed LED source running at about 330 pulses/second), and a high-speed boxcar integrator that detects and stores the fluorescence photon signal for each pulse. Moreover, the novel system uses multiple excitation beams and double-pass collection optics to increase the fluorescence signal. This combination enhances the sensitivity of the novel laser-induced-fluorescence system by two to three orders of magnitude over conventional spectrofluorometers, depending upon the spectrometer and optical detector configuration used.

The fluorescence measurements are performed using the novel system 10 depicted in the schematic diagram of FIG. 1. The light source may be microchip laser 12 or 14, 266 nm or 355 nm, respectively (JDS Uniphase, Models NU-10110-100 and NV-10110), or LED 13 operating at 265 nm, 300 nm, 335 nm or 355 nm (Sensor Electronic Technology, Inc., UVTOP® series). LED driver 13a is in electrical communication with LED 13 and oscilloscope 13b.

Silicon APD photodetector 15 (New Focus, Model 1621) is used to trigger data acquisition with the laser source. The LEDs are software-triggered. The laser beam is passed through optical quartz sample cell 16 (Spectrocell Inc., Model RF-3010-F) several times, for which plane mirrors 18a, 18b on the sides of the cell are used. The fluorescence signal is collected at a right angle to the excitation beam with concave mirror 20 (Optosigma, Model 035-0130) and a fused silica lens 22 (Optosigma, Model 014-0490). The fluorescent signal is passed through one of the bandpass optical filters contained within filter wheels 30, ranging from 265 nm to 685 nm, before being focused onto PMT 26 (Hamamatsu, Model H6780-03). A single filter wheel can hold up to eight (8) filters.

One of the absorption cut-off filters 30 (CVI Laser, Models CG-WG-280-2.00-2 and CG-WG-295-2.00-2) is used to block Rayleigh and Raman scattering. All filters are mounted on a stack of motorized filter wheels 30 (CVI Laser, Models AB-302 and AB-304). The PMT signal is acquired by gated integrator and boxcar averager unit 32 (Stanford Research System, Model SR-250). Data collection and filter wheel control is handled by LabVIEW software through computer interface unit 34 (Stanford Research System, Model SR-245) and serial bus.

Lasers 12 and 14 are Q-switched microchip lasers that generate output light pulses having duration of 0.4 ns, output light pulse energy of 0.3-0.4 µJ, and repetition rate of 8 kHz. The beam size is about one millimeter (1 mm)

Figure 2:
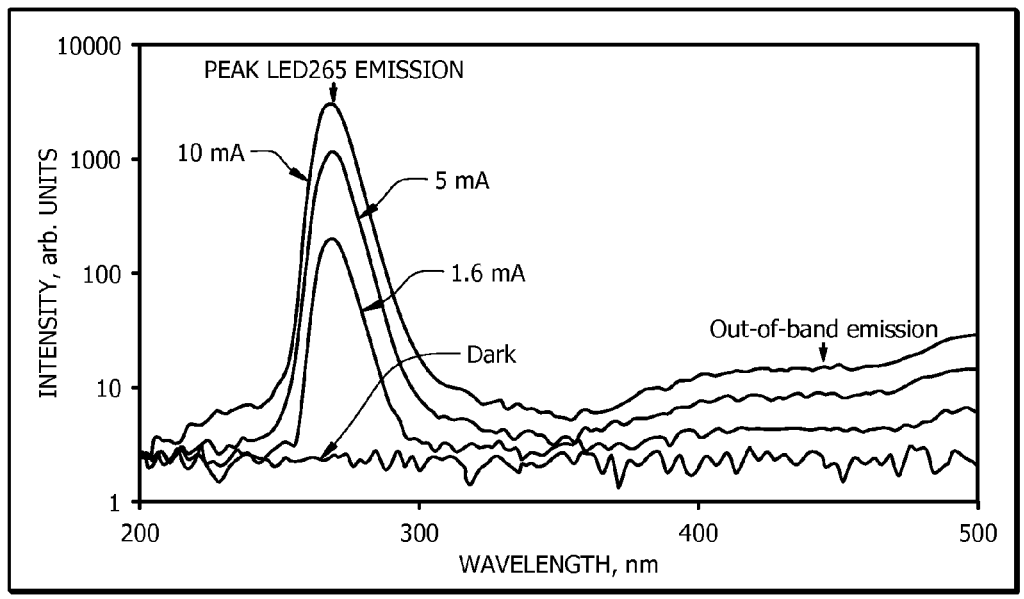
FIG. 2 depicts emission spectra of LED 265 for different CW currents and shows out-of-band emission.

LEDs 13 generate output light pulses having duration of 10 µs, drive current of 50 mA, and 330 Hz repetition rate. The output light pulse energy is approximately 7 nJ (with the exception of 22 nJ for the 355 nm LED). The LEDs have an out-of-band emission in the visible region. FIG. 2 depicts the measured output power of the 265 nm LED (LED265) as a function of wavelength and of drive current. FIG. 2 is a log plot of the intensity and shows that the out-of-band LED emission has a peak value of about one per cent (1%) compared to the peak emission at 265 nm.

To block the out-of-band light, a VIS-blocking, UV-passing filter (CVI Model CG-UG-11) is used with the LED sources.

Figure 3:
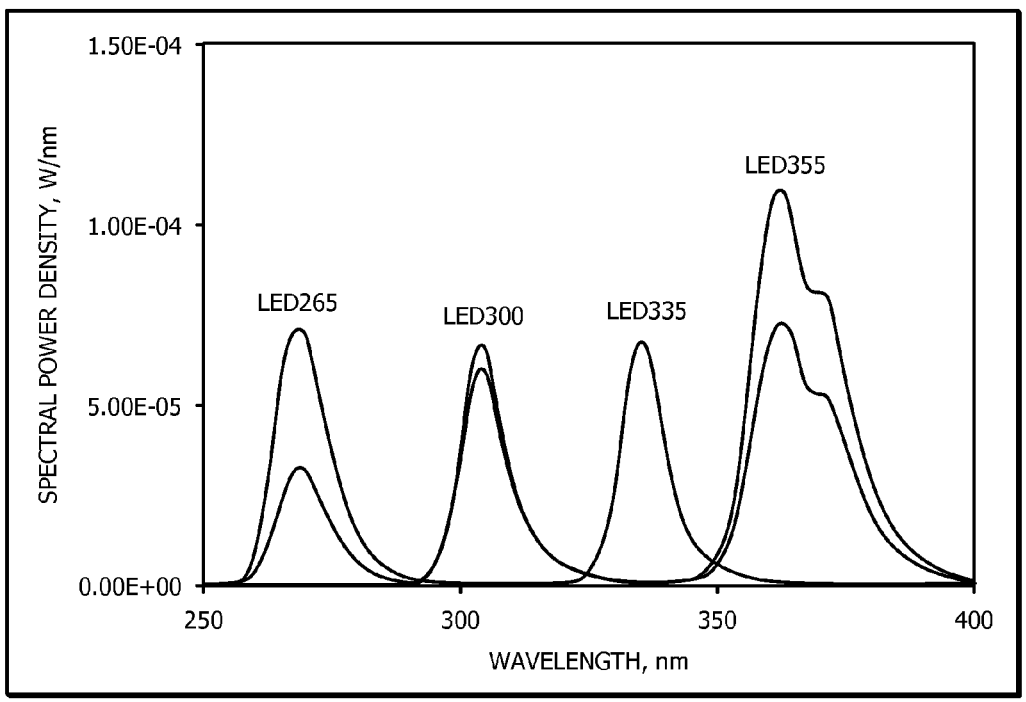
FIG. 3 depicts LED spectral peak power density in a 50 mA, 10 µs pulse regime (lower curves with CG-UG-11 filter used to eliminate out-of-band emission)

FIG. 3 depicts the spectral output power of the LEDs with and without the filter using a linear scale for the intensity. The beam size within the sample cell is about 5 mm.

The novel LIF system is used to measure a considerable variety of water related liquids including tap water, reverse osmosis (RO) treated ground water, and other water quality related substances.

Liquid samples are stored, when necessary, in the dark and are maintained at cold temperatures. Water samples are not further processed. Wine samples are diluted to 10 mL per liter with distilled water. Humic substances (International Humic Substances Society, 1R101N, 1S103H, 1S104H) are prepared as 10 mg per 500 mL of distilled water.

A flow cell with a linear flow rate of five centimeters per second (5 cm/s) is used to minimize photobleaching. One thousand (1000) measurements are taken with each bandpass filter. These last a few seconds per filter setting including filter switching time. The boxcar averaging setting was three hundred (300) samples. The sensitivity setting is adjusted for each sample to maximize the signal. The spectra are compensated for filter bandwidth and transmission, PMT quantum efficiency and gating integrator/boxcar averager sensitivity.

Figure 4:
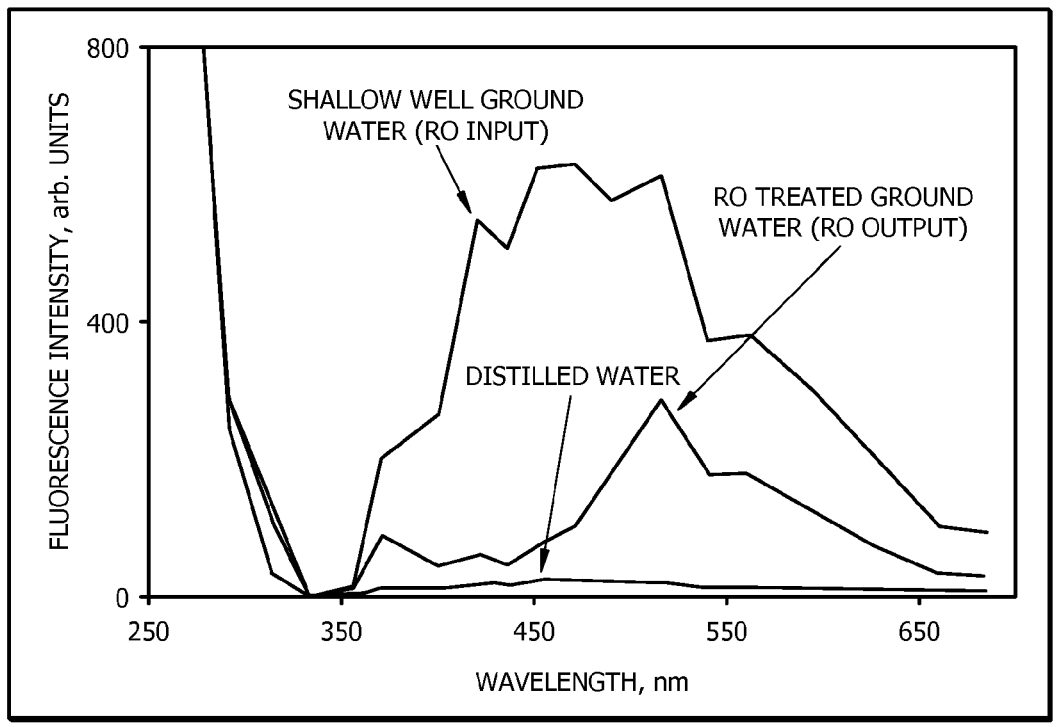
FIG. 4 depicts fluorescence of ground water before and after reverse osmosis treatment at a laser excitation of 266 nm.

Ground water taken from a shallow well at the University of South Florida (USF) was processed by a reverse osmosis unit. The fluorescence spectra of ground water before and after RO treatment using 266 nm laser excitation is shown in FIG. 4. The broad peak observed around 470 nm in the untreated water is typical of the organic compounds usually present in such samples (Coble, 2007). After the RO treatment, the fluorescence signal decreased significantly, especially on the short-wavelength side. The signal from distilled water is shown for comparison.

Figure 5A:
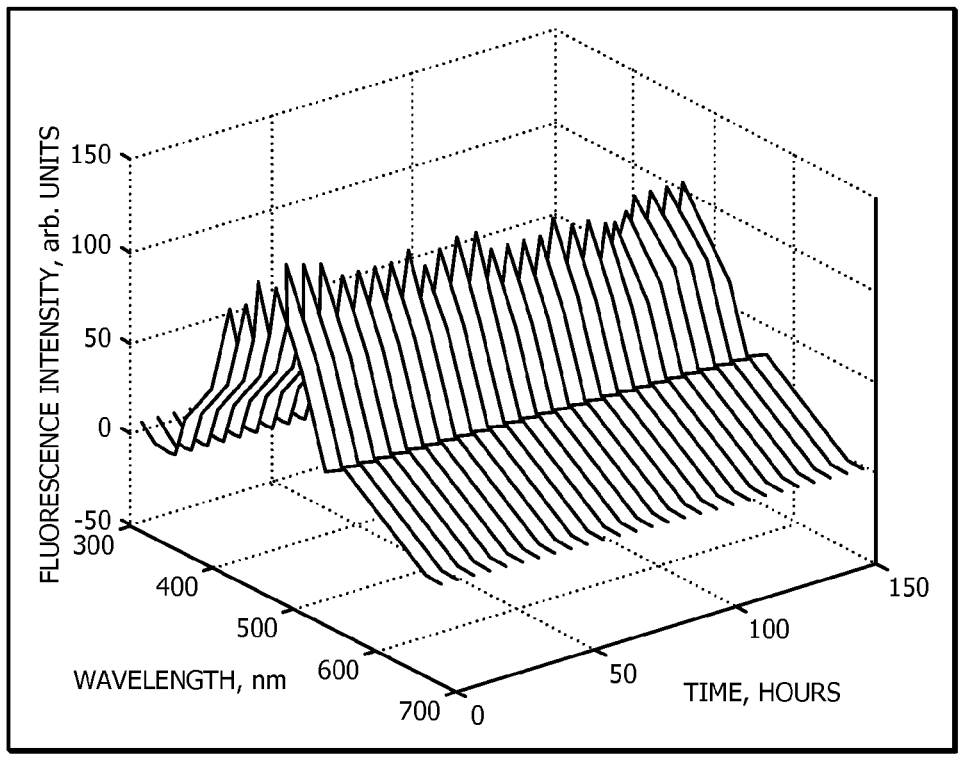
FIG. 5A depicts fluorescence of continuously running tap water, monitored for one week at a laser excitation of 266 nm.
Figure 5B:
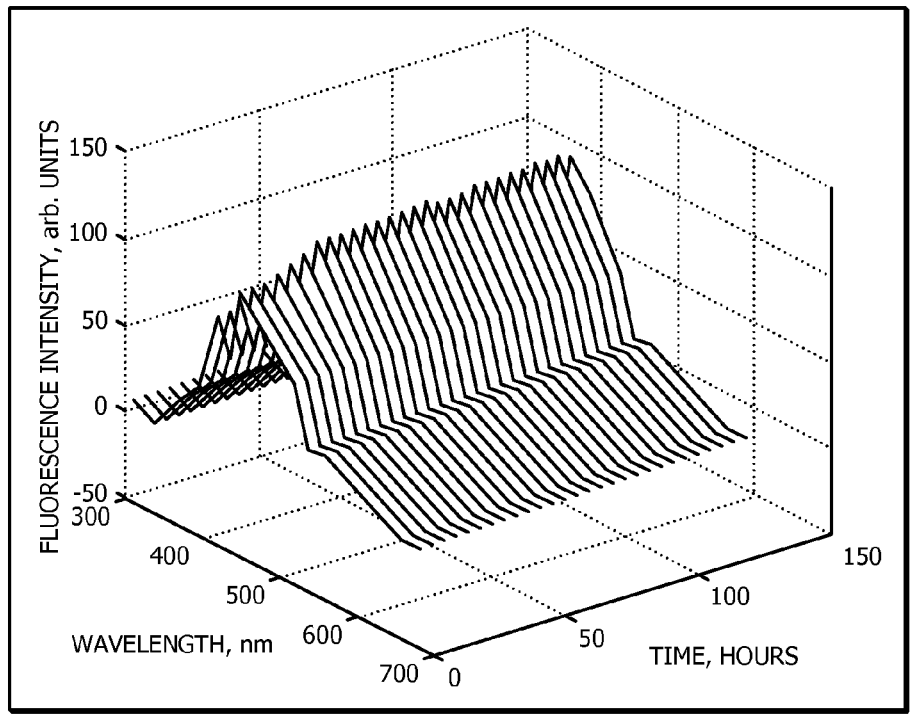
FIG. 5B depicts fluorescence of re-circulated tap water, monitored for one week at a laser excitation of 266 nm.

Tap water was continuously monitored for a period of a week. FIG. 5A indicates that the fluorescence of flowing tap water has a greater range of variation than a sample re-circulated through the system, as depicted in FIG. 5B. Certain repetitiveness of the running water signal might be indicative of the water usage patterns at USF. The initial growth in the re-circulated signal is due to plastic leaching from the soft tubing used in the pump.

Figure 6A:
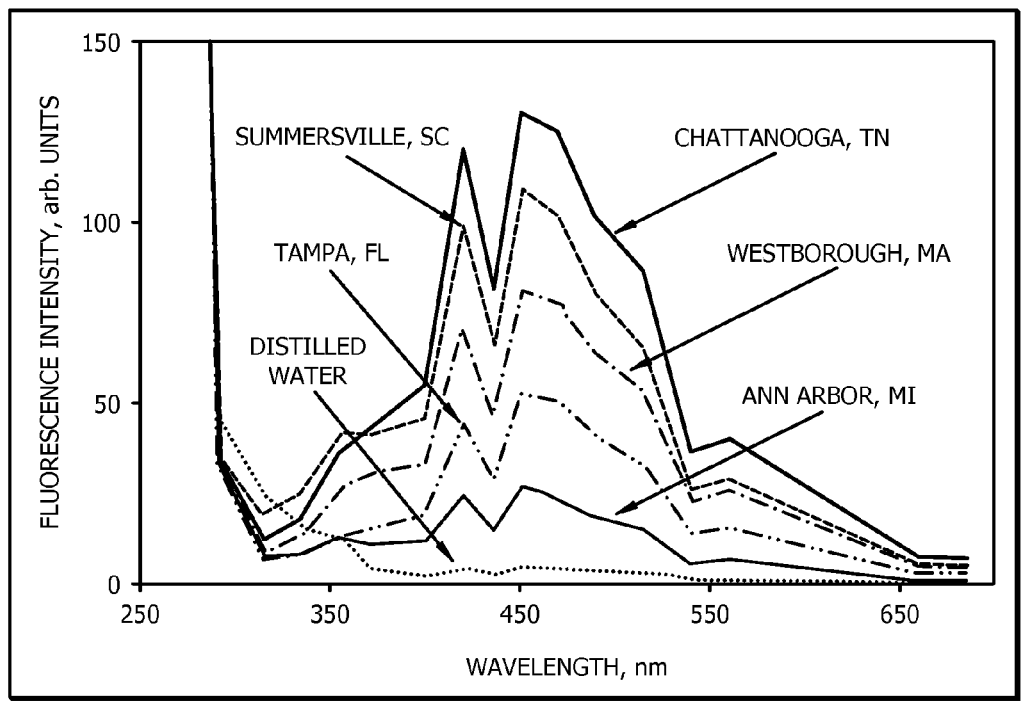
FIG. 6A depicts fluorescence of tap water with a laser excitation of 266 nm.
Figure 6B:
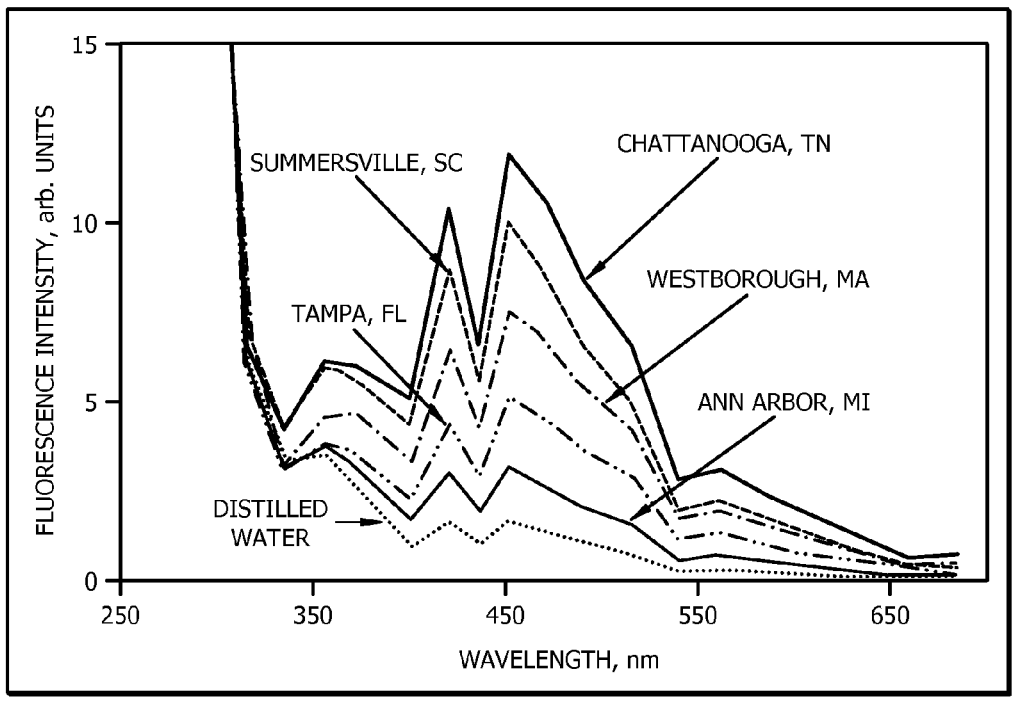
FIG. 6B depicts fluorescence of tap water with LED excitation of 265 nm.

The results of tap water collected from different locations in the U.S. are depicted in FIGS. 6A and 6B. All samples were taken directly from residential tap water except for the Tampa location, where an on-line water filter in a drinking fountain was present. For all samples, settings were the same during data acquisition. FIGS. 6A and 6B respectively indicate that the fluorescence spectra obtained with 266 nm laser excitation and 265 nm LED are different only in overall intensity. Comparing the spectra from different locations, all possess two large peaks centered around 420 and 460 nm, as well as smaller peaks on the sides. However, both the absolute and relative intensity of the peaks varies with the location, thereby indicating that the difference in both the total concentration and the species of organic compounds are present in the sample.

The signal-to-noise ratio (SNR) was calculated for the set of tap water samples as a difference between peak fluorescence of the sample and the distilled water (reference) signals divided by double the standard deviation of one thousand (1000) measurements. The results were typically in the 300-900 range for the laser sources, and around 30-190 for the LEDs. For example, at 266 nm, the laser pulse energy was about 100 times greater than the LED pulse energy, but the SNR values differed only by a factor of 10, i.e., being about 296 for the laser LIF and about 26 for LED excitation for the Ann Arbor water data. The reason for the stronger than expected signal with the LED excitation may be due to differences in the light excitation and fluorescence overlap volume in the LED configuration or sample photobleaching in the case of the lasers.

The novel LIF system also detects long-term changes in the fluorescence of total organic carbon (TOC) and the influence of chlorine on TOC fluorescence. Tannic acid, a specific type of tannin (plant polyphenol), is often used to represent TOC in water analysis measurements. Distilled water and trace solutions of organic compounds were re-circulated in the portable LIF system for several hours. Tannic acid representing total organic carbon (3 mg/L in deionized water) and chlorinated tannic acid (3 mg/L TOC and 12 mg/L Cl in deionized water) samples were prepared from a water processing laboratory. The solutions were produced by dilution of pure chemicals in nanopure deionized water. Concentrations of TOC and chlorine in the samples shown in FIGS. 6A and 6B are typical of those in drinking water.

Figure 7:
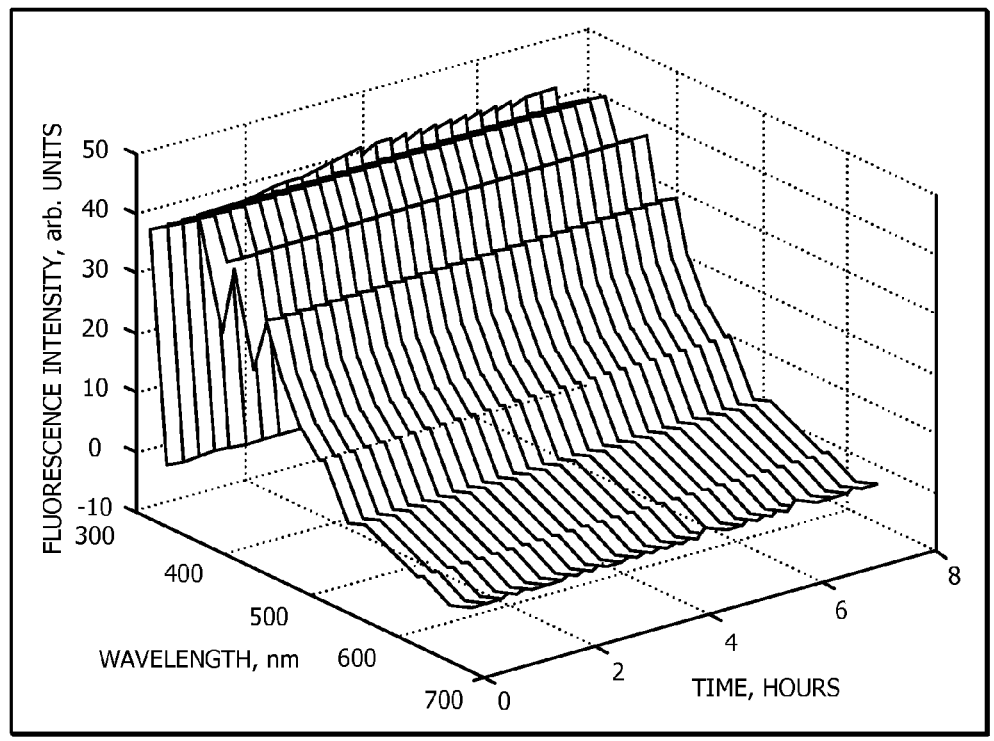
FIG. 7 depicts fluorescence of tannic acid over seven (7) hours of continuous monitoring at a laser excitation of 266 nm.

The LIF signal for a sample of tannic acid is shown in FIG. 7 and was obtained using the 266 nm laser. The fluorescence in FIG. 7 has the strongest peak at 370 nm, the second-strongest at 420 nm, and a weaker peak at 451 nm. This is quite distinct from the typical natural fluorescence of water, for example FIG. 6A, which indicates a broad peak maximized at 451 nm.

Figure 8:
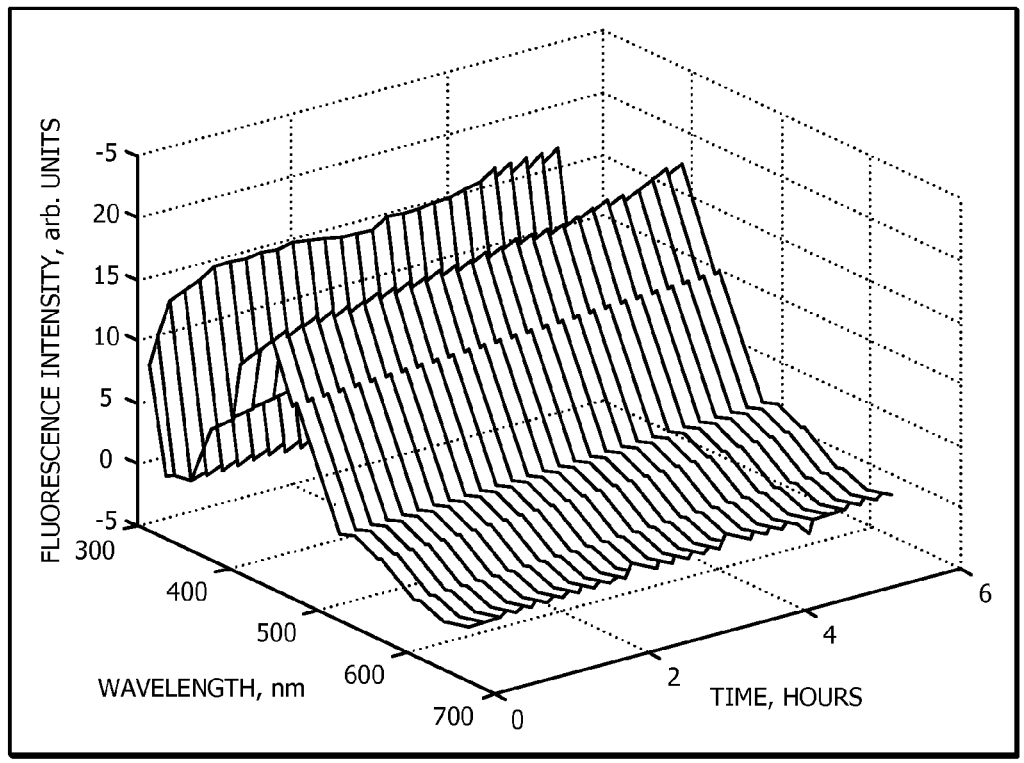
FIG. 8 depicts fluorescence of tannic acid and chlorine over five (5) hours of continuous monitoring at a laser excitation of 266 nm.

Fluorescence of a solution containing both tannic acid and chlorine is shown in FIG. 8 for 266 nm excitation. The solution was re-circulated for about five (5) hours. The spectrum for the 266 nm excitation is significantly different from that of tannic acid alone. The peak at 370 nm is completely suppressed, and the 420 nm peak is reduced drastically. The strongest fluorescence is observed at 451 nm.

Figure 9A:
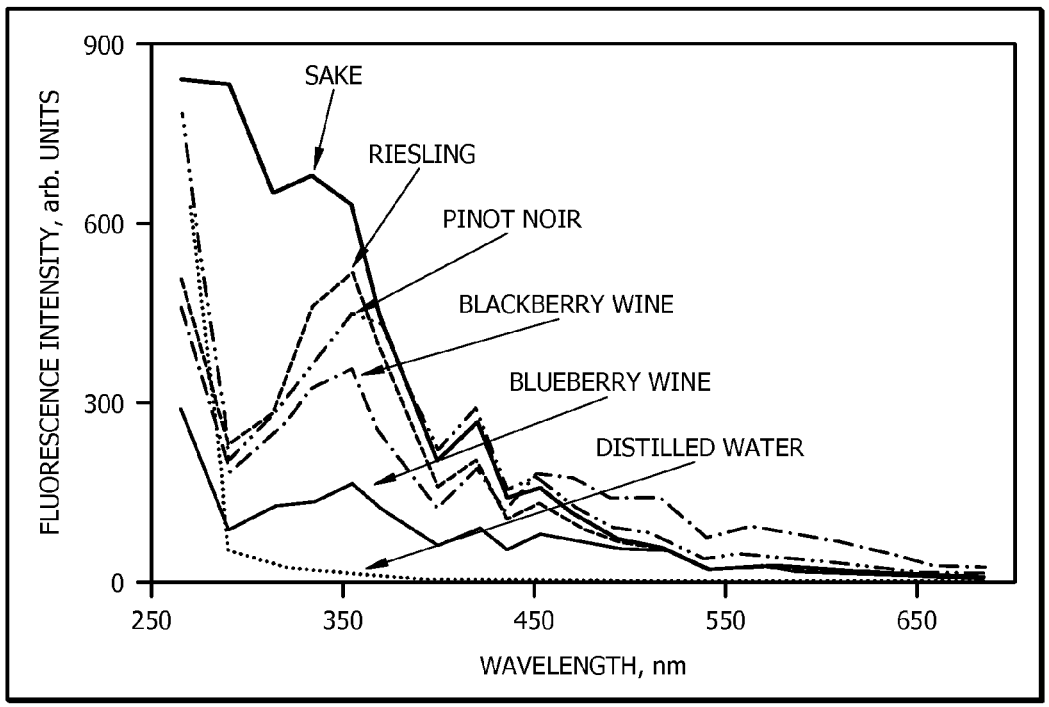
FIG. 9A depicts the fluorescence of wine samples with a laser excitation of 266 nm.
Figure 9B:
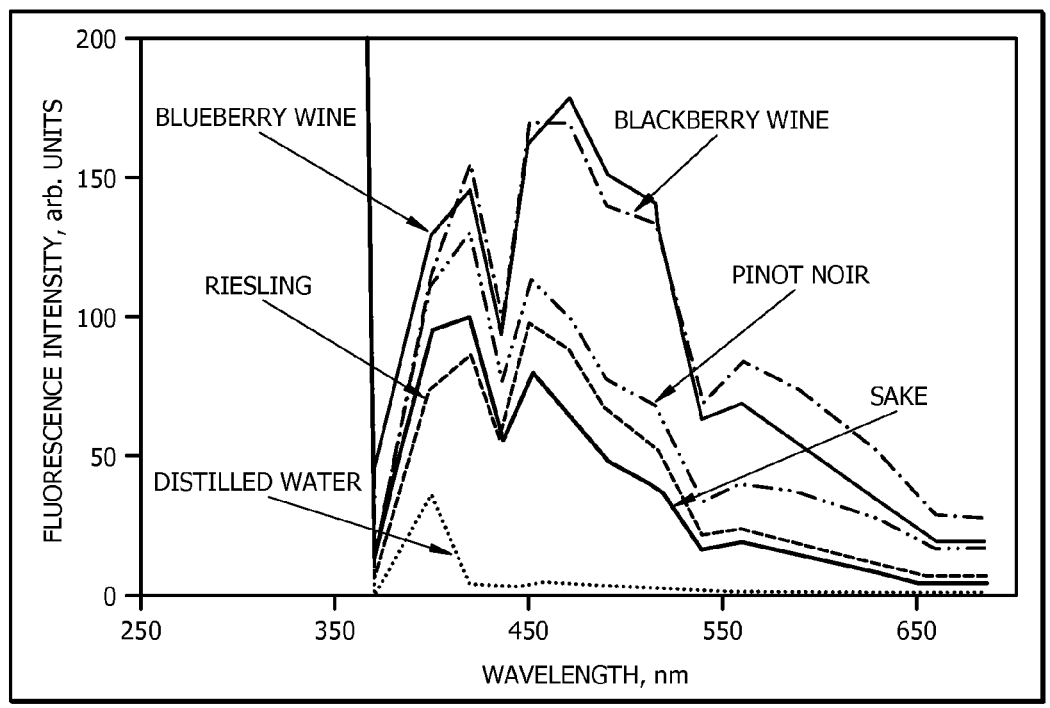
FIG. 9B depicts the fluorescence of wine samples with a laser excitation of 355 nm.
Figure 10A:
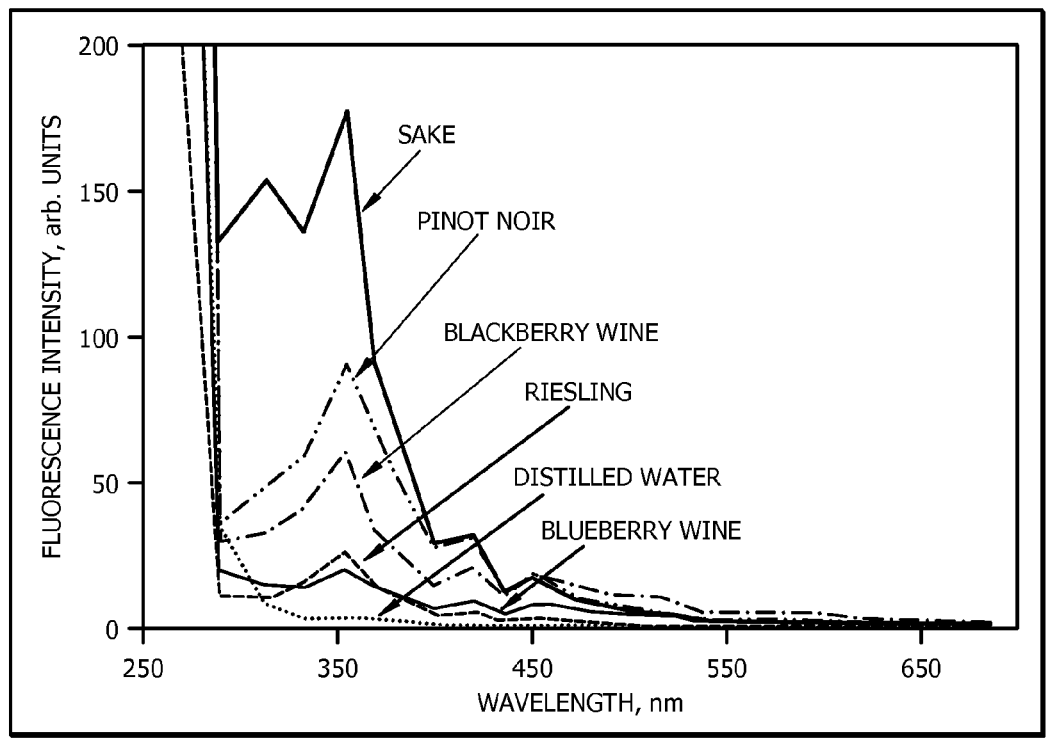
FIG. 10A depicts the fluorescence of wine samples with an LED excitation of 266 nm.
Figure 10B:
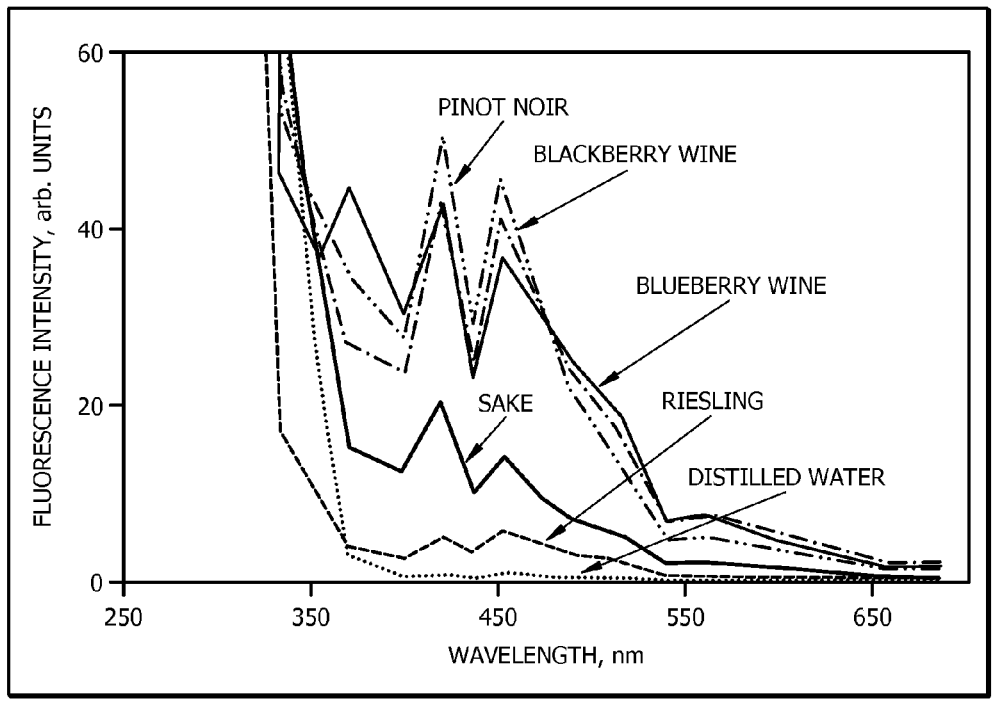
FIG. 10B depicts the fluorescence of wine samples with an LED excitation of 300 nm.
Figure 10C:
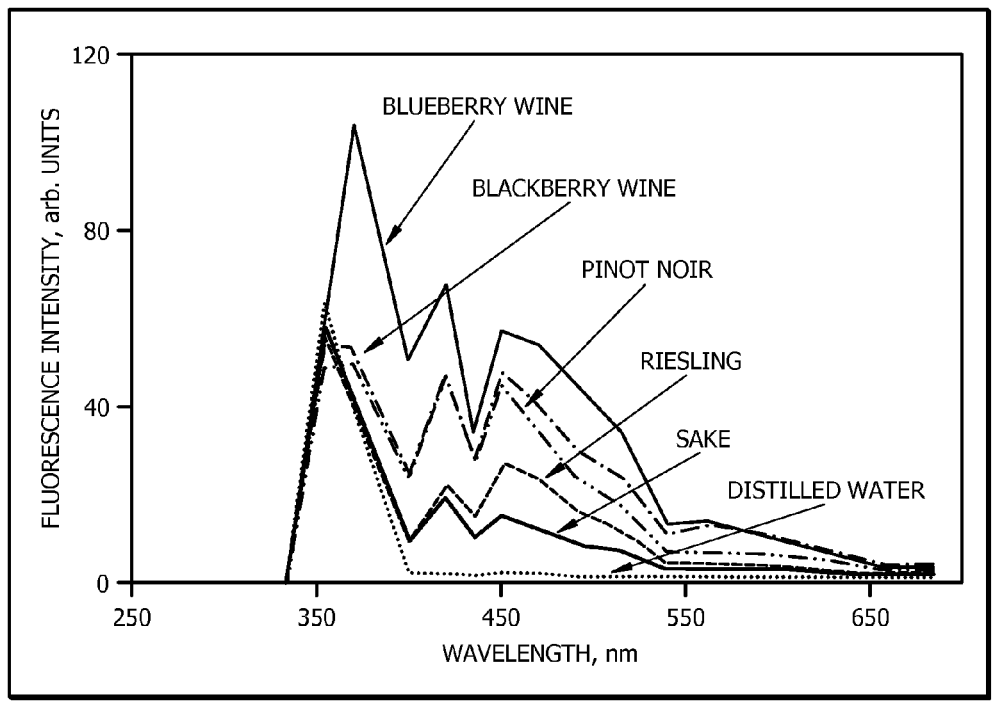
FIG. 10C depicts the fluorescence of wine samples with an LED excitation of 335 nm.
Figure 10D:
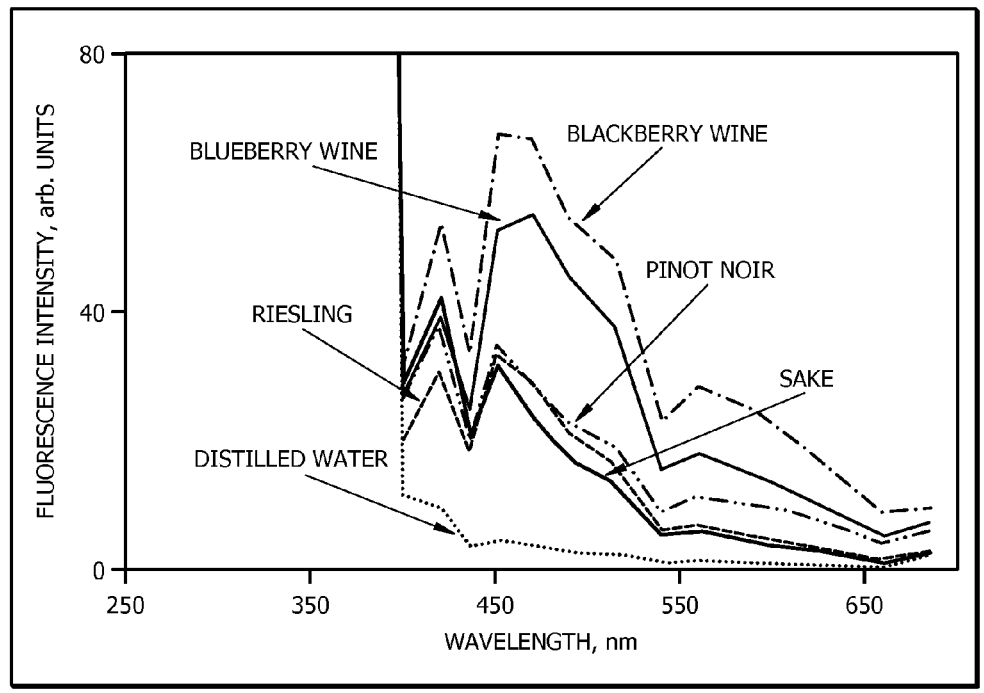
FIG. 10D depicts the fluorescence of wine samples with an LED excitation of 355 nm.

Several types of wine were diluted to ~1% with distilled water to minimize absorption and scattering in the sample cell. All spectra were taken under the same settings and conditions. Fluorescence spectra of these wine samples are shown in FIGS. 9A and 9B (laser excitation) and FIGS. 10A and 10B (LED excitation).

Comparing wine spectra (FIGS. 9A and 9B) with those of tap water (FIGS. 6A and 6B), there is a difference in intensity and in the shape of the spectrum, particularly at 266 nm excitation. The emission peak at 350 nm dominates in the wine spectra of FIG. 9A using 266 nm excitation, but is possibly hidden by the scattering of the 355 nm excitation laser in FIG. 9B.

As indicated in FIGS. 9A, 9B and FIGS. 10A, 10B, there is also a significant dependence on the excitation wavelength for the wine samples. For example, at 266 nm excitation, the signal from sake is strongest, while fruit wines exhibit greater fluorescence at longer excitation wavelengths.

The laser and LED-excited fluorescence spectra are generally consistent. The Riesling wine is exceptional because it shows a much weaker secondary emission peak near 450 nm when the 265 nm LED is used as the light source. This might be due to the difference in the overlap between the sample absorption and the excitation line width, or it may be another indication of strong scattering at this excitation wavelength.

Figure 11:
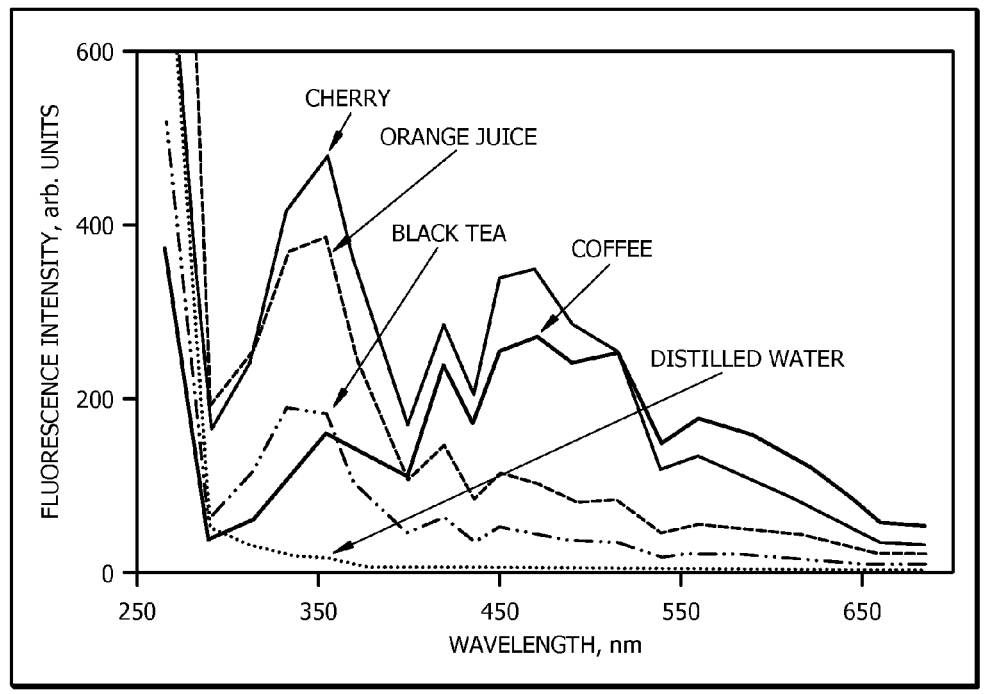
FIG. 11 depicts the fluorescence of various drinks and distilled water at a laser excitation of 266 nm.

The novel LIF system for other drinkable liquids such as coffee and orange juice was also studied. Some of the results are shown in FIG. 11 using diluted samples. The data shows strong fluorescence emission near 350 nm and near 450 to 470 nm.

Figure 12A:
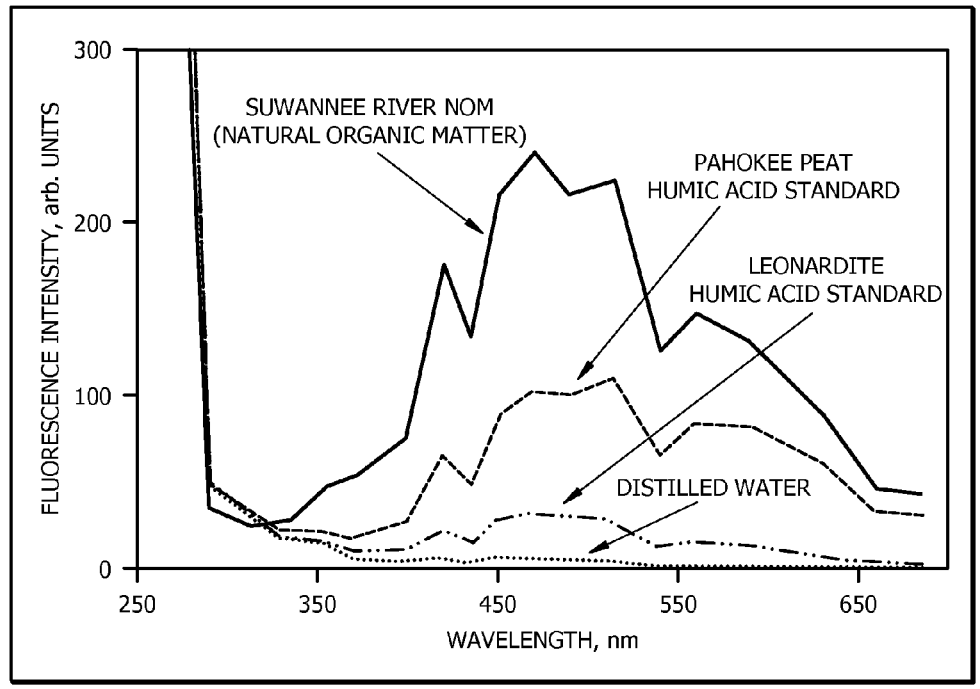
FIG. 12A depicts the fluorescence of humic substances at a laser excitation of 266 nm.
Figure 12B:
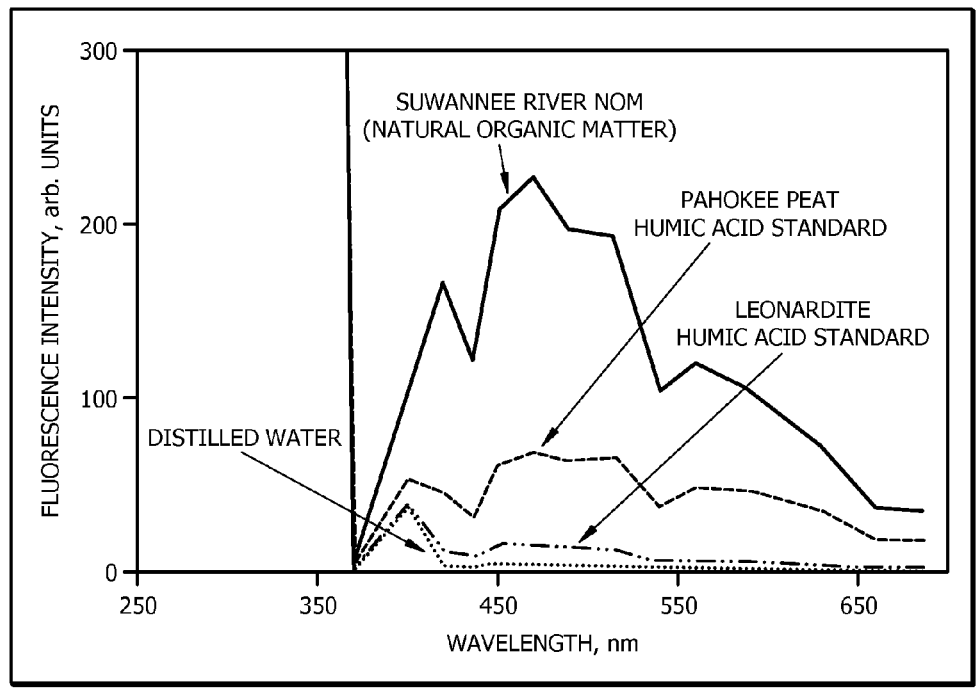
FIG. 12B depicts the fluorescence of humic substances at a laser excitation of 355 nm.
Figure 13A:
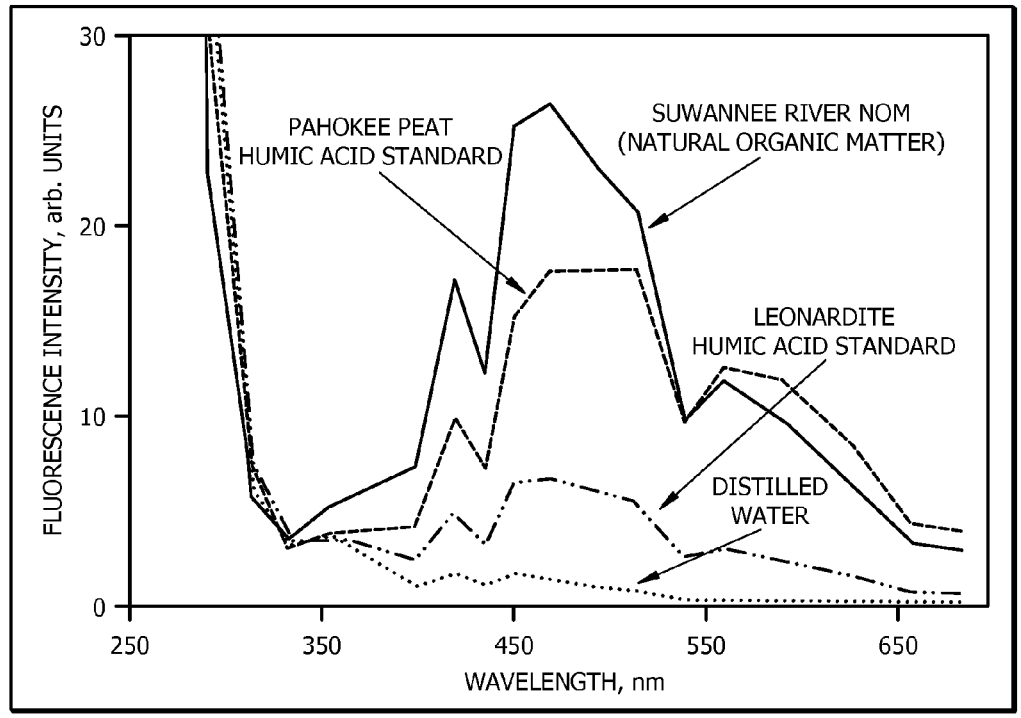
FIG. 13A depicts fluorescence of humic substances at an LED excitation of 266 nm.
Figure 13B:
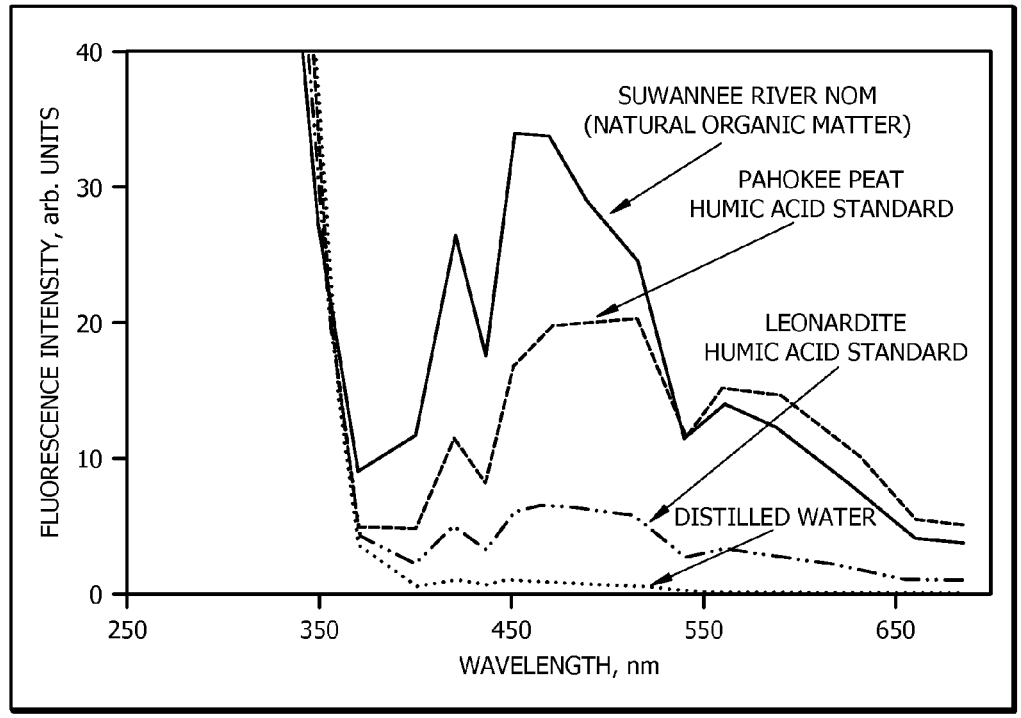
FIG. 13B depicts fluorescence of humic substances at an LED excitation of 300 nm.
Figure 13C:
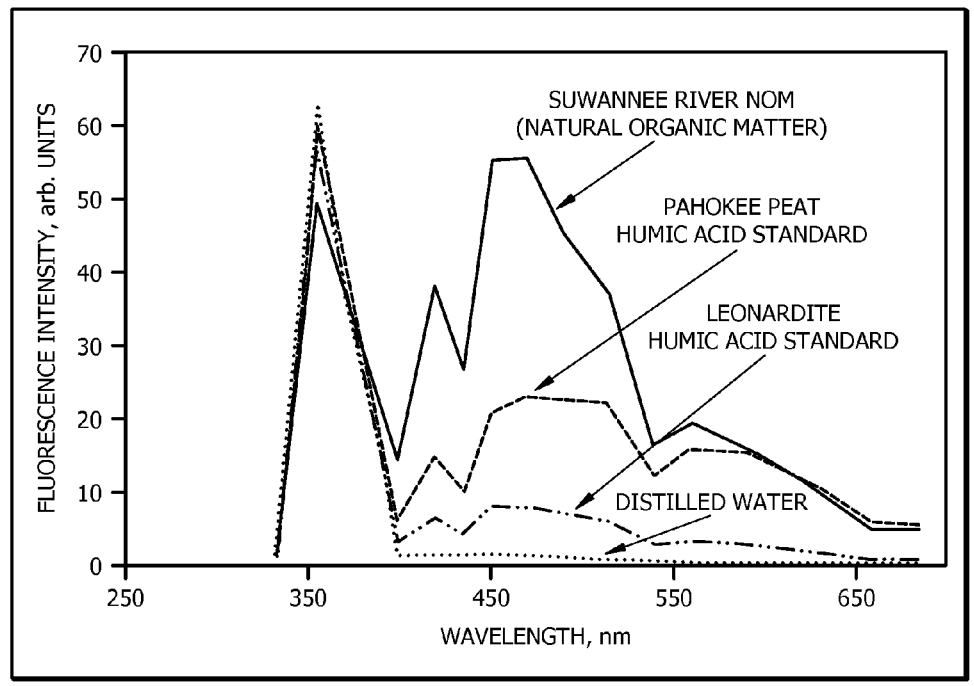
FIG. 13C depicts fluorescence of humic substances at an LED excitation of 335 nm.
Figure 13D:
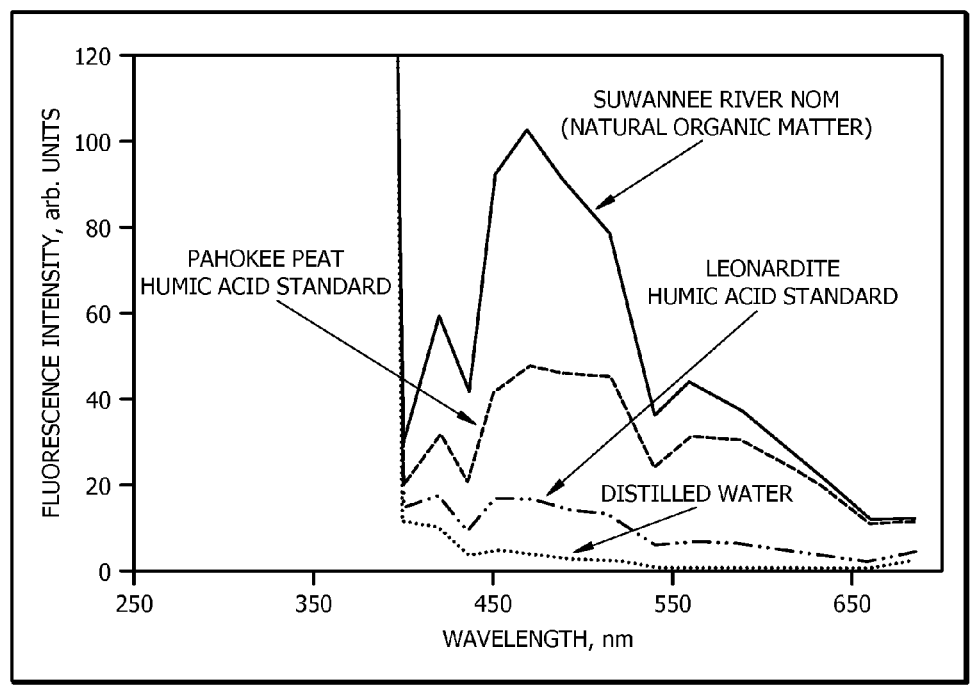
FIG. 13D depicts fluorescence of humic substances at an LED excitation of 355 nm.

Humic acid is a principal component of humic substances, which are the major organic constituents of soil, humus, peat, coal, many upland streams, natural lakes, and ocean water. It is usually produced by biodegradation of dead organic matter. Samples of humic acid standards and natural organic matter were obtained from the International Humic Substances Society (ihss.gatech.edu). FIGS. 12A and 12B show fluorescence spectra of these substances with laser excitation and FIGS. 13A-13D with LED excitation. The data is in general agreement with excitation-emission spectroscopic properties of these materials as reported on the IHSS website (ihss.gatech.edu/spectra.html). The spectral peaks occur near 450 nm and 500 nm for these humic acid samples. Shifts in aged humic samples with fluorescence peaks gravitating toward the 500 nm wavelengths were observed in the prior art and the results obtained by the novel system are consistent with the earlier findings.

A compact version of the novel LIF system using a conventional compact spectrometer to replace the set of optical filters for fluorescence wavelength selection also has utility. Such a system is several orders of magnitude lower in sensitivity than the system disclosed in FIG. 1, but the compact design and ease of use has many advantages especially for those cases where the concentration of the DOCs or CDOM is high.

Figure 14:
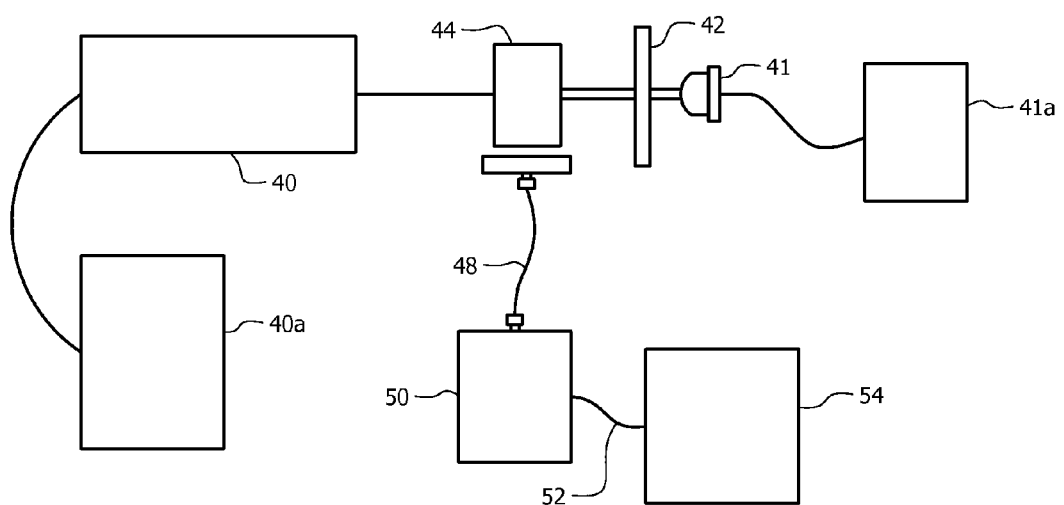
FIG. 14 is a schematic diagram of the novel compact CW laboratory bench-top LED-IF/LIF system.

FIG. 14 is a schematic diagram of the novel laboratory bench-top LED-IF/LIF non-optimized compact system. Microchip 266 nm laser 40 is in electrical communication with laser power supply 40a. Alternatively, UV LED 41 equipped with VIS-blocking CG-UG-11 filter 42 and being in electrical communication with LED driver and power supply 41a may be used interchangeably with said laser 40 to illuminate sample-containing quartz cell 44. Fluorescence emission is passed through UV-blocking filter 46 to eliminate the second-order peak of the scattered excitation wavelength, and is collected at ninety degrees)(90° by an optical fiber 48 connected to compact spectrometer 50, commercially available from Ocean Optics, Inc., (Model USB2000). USB cable 52 provides electrical communication between the output of spectrometer 50 output and PC 54.

FIG. 14 is a composite figure in that it shows how the laser and LED can be compared with each other. In practice, one or the other would be used. Fluorescence of natural and drinking water samples were recorded using the system disclosed in FIG. 14 to compare the signal-to-noise ratio with the laser and LED excitation, and to determine the feasibility of continuous wave (CW) LED sources in this compact setup. Lake water with its strong CDOM fluorescence was tested first, and then examples of drinking water were studied as well.

Figure 15:
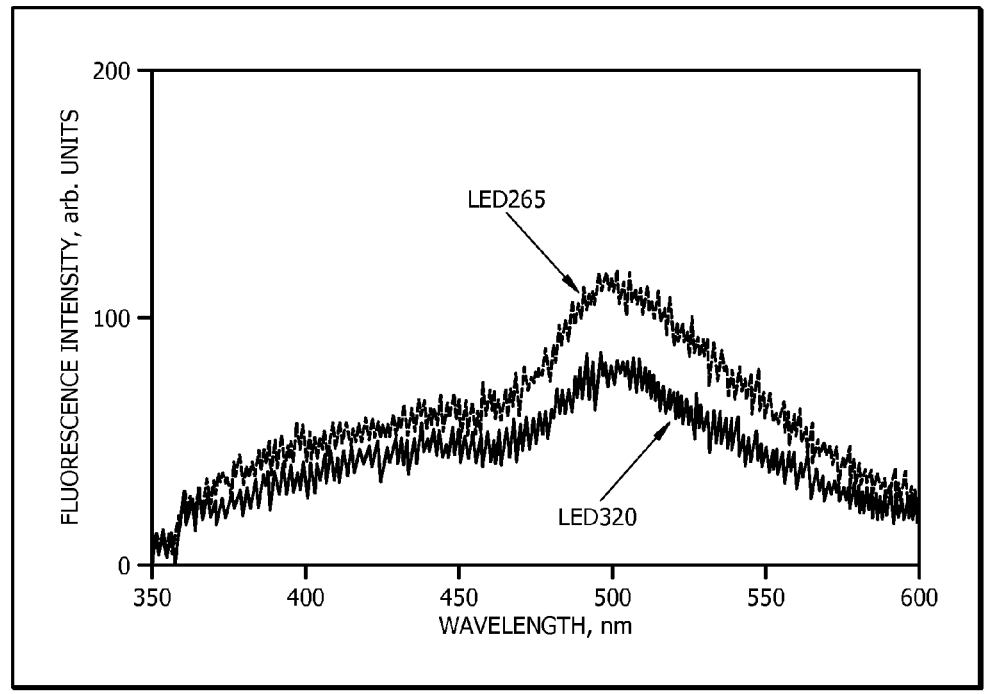
FIG. 15 depicts lake water fluorescence at LED excitation of 265 nm and 320 nm LED excitation, employing a UV-blocking filter.

FIG. 15 shows the fluorescence emission from lake water. The emission peak is near 500 nm, and is shifted somewhat from that observed for the tap water samples disclosed in FIGS. 6A and 6B. The fluorescence signal is weak but the system and optical collection efficiency can be improved.

Figure 16:
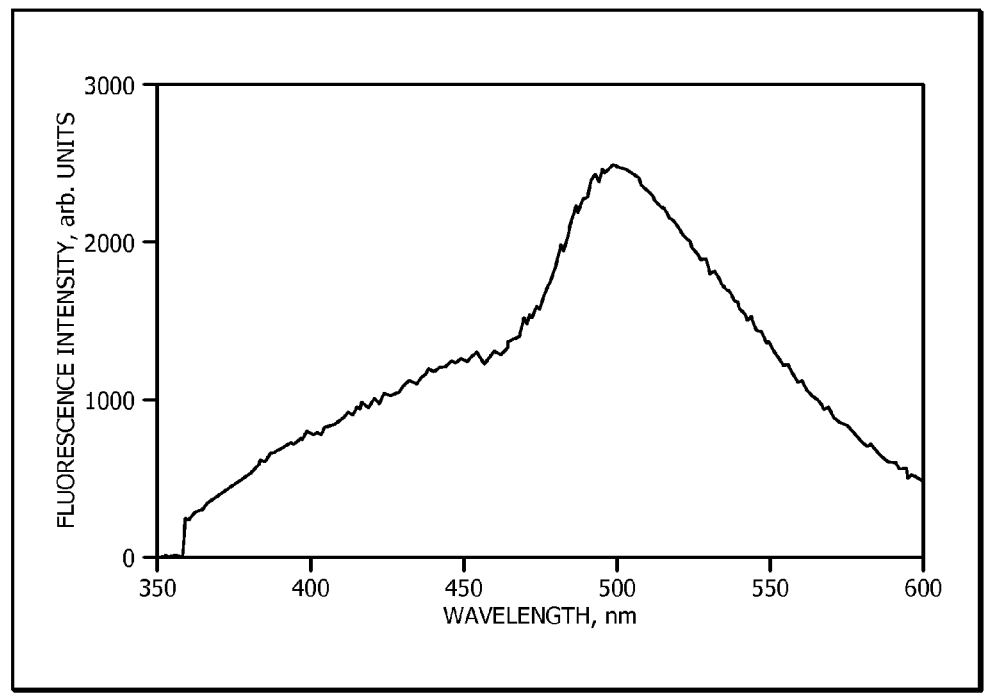
FIG. 16 depicts lake water fluorescence at a laser excitation of 266 nm, employing a UV-blocking filter.

FIG. 16 depicts a similar LIF spectrum for lake water, using a 266 nm laser source. The spectral features are similar, but the SNR is higher.

The novel laser and LED-induced fluorescence system provides the spectra of organic contaminants in drinking water and other liquids. Spectra obtained using LED and laser excitation at the same wavelength exhibits great similarity, while differing in overall intensity. Greater than expected SNR observed with LED excitation indicates that a compact, less expensive LED based system has utility for detection or monitoring, or both, of trace organics and appropriate species in these liquids. Deep-UV LIF spectroscopy offers advantages for measurements of trace species in water in real time. In some cases the fluorescence spectrum is unique, but in many cases similar spectral peaks are observed. In the latter case, the novel LIF system may not be suitable for selective discrimination and identification of different trace species in water, but has utility in real time monitoring of a known substance if correctly calibrated.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between.

What is claimed is:

1. An apparatus for measuring fluorescence of potable liquids, comprising:
    a deep-UV light source that generates a light beam;
    an optical quartz cell;
    said optical quartz cell being disposed between a pair of plane mirrors so that light from said light source travels through said optical quartz cell several times;
    a photodetector;
    a concave mirror for collecting a fluorescence signal;
    said concave mirror having an optical axis disposed normal to an optical axis of said light beam;
    a lens having an optical axis disposed normal to said optical axis of said light beam;
    said concave mirror and said lens being positioned on opposite sides of said optical quartz cell;
    a fluorescence detector disposed in optical alignment with said concave mirror and said lens;
    a gated integrator and boxcar averager disposed in electrical communication with said fluorescence detector;
    an oscilloscope in electrical communication with said gated integrator and boxcar averager;
    a data acquisition computer in electrical communication with said gated integrator and boxcar averager;
    whereby said data acquisition computer acquires fluorescence data from said quartz sample cell; and
    whereby said oscilloscope provides visual images of said fluorescence data from said quartz sample cell.

2. The apparatus of claim 1, further comprising:
    said light source being a microchip laser generating output light pulses having a wavelength of 266 nm, having a duration of about 0.4 ns, an output light pulse energy of about 0.3-0.4 µJ, a repetition rate of 8 kHz, and having a beam size of about one millimeter.

3. The apparatus of claim 1, further comprising:
said light source being a microchip laser generating output light pulses having a wavelength of 355 nm, having a duration of about 0.4 ns, an energy of about 0.3-0.4 µJ, a repetition rate of 8 kHz, and having a beam size of about one millimeter.

4. The apparatus of claim 1, further comprising:
said light source being an LED generating output light pulses having a wavelength of 265 nm, a duration of 10 µs, an output light pulse energy of about 7 nJ, a repetition rate of 330 Hz, a drive current of 50 mA, and an out-of-band emission in the visible region.

5. The apparatus of claim 1, further comprising:
said light source being an LED generating output light pulses having a wavelength of 300 nm, a duration of 10 µs, an output light pulse energy of about 7 nJ, a repetition rate of 330 Hz, a drive current of 50 mA, and an out-of-band emission in the visible region.

6. The apparatus of claim 1, further comprising:
said light source being an LED generating output light pulses having a wavelength of 335 nm, a duration of 10 µs, an output light pulse energy of about 7 nJ, a repetition rate of 330 Hz, a drive current of 50 mA, and an out-of-band emission in the visible region.

7. The apparatus of claim 1, further comprising:
said light source being an LED generating output light pulses having a wavelength of 355 nm, a duration of 10 µs, an output light pulse energy of about 22 nJ, a repetition rate of 330 Hz, a drive current of 50 mA, and an out-of-band emission in the visible region.

8. The apparatus of claim 4, further comprising:
at least one UV-blocking, visible transmitting optical filter to reduce and eliminate the out-of-band emission from the LED to reduce interference at the subsequent fluorescence emission wavelength.

9. The apparatus of claim 1, further comprising:
at least one bandpass optical filter disposed between said collection lens and said fluorescence detector;
said at least one bandpass optical filter having a range of 265 to 685 nm.

10. The apparatus of claim 9, further comprising:
at least one absorption cut-off filter disposed between said collection lens and said fluorescence detector;
said at least one absorption cut-off filter adapted to block Rayleigh and Raman scattering.

11. The apparatus of claim 10, further comprising:
a stack of motorized filter wheels for rotatably supporting said at least one bandpass optical filter and said at least one absorption cut-off filter.

12. The apparatus of claim 11, further comprising:
a compact spectrometer and optical detector.

* * * * *

UNITED STATES PATENT AND TRADEMARK OFFICE
CERTIFICATE OF CORRECTION

| | | |
|---|---|---|
| PATENT NO. | : 8,467,059 B2 | Page 1 of 1 |
| APPLICATION NO. | : 12/887948 | |
| DATED | : June 18, 2013 | |
| INVENTOR(S) | : Dennis K. Killinger, Anna Sharikova and Vasanthi Sivaprakasam | |

It is certified that error appears in the above-identified patent and that said Letters Patent is hereby corrected as shown below:

In the Specification

Col. 1, Line 5, please add the following:

STATEMENT OF GOVERNMENT INTEREST

This invention was made with U.S. government support under Grant No. W911NF-05-1-0431 awarded by the U.S. Army Research Office and Grant No. N00014-04-1-0555 awarded by the U.S. Office of Naval Research. The U.S. government has certain rights in the invention.

Signed and Sealed this
Nineteenth Day of November, 2013

Teresa Stanek Rea
*Deputy Director of the United States Patent and Trademark Office*